United States Patent [19]

Löher et al.

[11] Patent Number: 5,521,143
[45] Date of Patent: May 28, 1996

[54] PLANT-PROTECTING AGENTS CONTAINING ISOXAZOLINES OR ISOTHIAZOLINES, AND NOVEL ISOXAZOLINES AND ISOTHIAZOLINES

[75] Inventors: Heinz-Josef Löher, Liederbach; Klaus Bauer, Hanau; Hermann Bieringer, Eppstein/Taunus, all of Germany

[73] Assignee: Hoechst Aktiengesellschaft, Frankfurt, Germany

[21] Appl. No.: 972,448
[22] PCT Filed: Aug. 8, 1991
[86] PCT No.: PCT/EP91/01503
  § 371 Date: Jan. 29, 1993
  § 102(e) Date: Jan. 29, 1993
[87] PCT Pub. No.: WO92/03053
  PCT Pub. Date: Mar. 5, 1992

[30] Foreign Application Priority Data

Aug. 17, 1990 [DE] Germany .................. 40 26 018.6

[51] Int. Cl.$^6$ .................. A01N 43/72; C07D 261/02
[52] U.S. Cl. .................. 504/106; 504/105; 504/269; 504/271; 548/214; 548/240; 548/110; 546/269.7; 546/271.4; 546/256; 544/133; 544/137
[58] Field of Search .................. 504/106, 269, 504/271; 548/214, 240; 546/275, 280; 544/133, 137

[56] References Cited

U.S. PATENT DOCUMENTS 4,144,047  3/1979  Franz et al. .................. 504/269
5,080,708  1/1992  Freund et al. .................. 548/104

FOREIGN PATENT DOCUMENTS 62-103070  5/1987  Japan .................. 548/240

OTHER PUBLICATIONS

CA 91: 15174n 3-Aryl-4-isoxazolecarboxylic . . . regulants. Franz et al., p. 194, 1979.
CA 107: 96708p Preparation . . . regulators. Oda et al. p. 692, 1987.
CA112: 235289w Preparation . . . herbicides. Freund et al., p. 194, 1990.

Primary Examiner—Joseph K. McKane
Attorney, Agent, or Firm—Curtis, Morris & Safford

[57] ABSTRACT

Isoxazolines or isothiazolines having the formula (I), or their salts, in which $(Z)_n$, X and R have the definition given in the first claim, are useful as safeners against the phytotoxic side effects of herbicides, preferably in cereal crops.

14 Claims, No Drawings

PLANT-PROTECTING AGENTS CONTAINING ISOXAZOLINES OR ISOTHIAZOLINES, AND NOVEL ISOXAZOLINES AND ISOTHIAZOLINES

The invention relates to safeners or antidotes which, in combination with herbicides, can reduce the phytotoxicity of the herbicides to crop plants.

The invention provides plant-protecting agents which contain isoxazolines or isothiazolines of the general formula I or salts thereof,

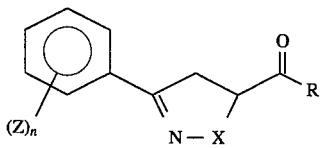

in which
X is an oxygen or sulfur atom, in particular an oxygen atom,
R is OH, SH, alkoxy, alkenyloxy, alkynyloxy, alkylthio, alkenylthio, alkynylthio, cycloalkyloxy or cycloalkylthio,
where the 8 last-mentioned groups are unsubstituted or mono- or polysubstituted by radicals from the group comprising phenyl, alkoxy, alkenyloxy, alkynyloxy, benzyloxy, phenyloxy, cycloalkyloxy, alkylthio, mono- and dialkylamino, cyano, halogen and $NO_2$,
or is benzyloxy, phenyloxy, benzylthio or phenylthio, where the 4 last-mentioned groups are unsubstituted or mono- or polysubstituted by radicals from the group comprising alkyl, alkenyl, alkynyl, halogen, cyano, $NO_2$, alkoxy, alkenyloxy, alkynyloxy, alkylthio, mono- and dialkylamino, phenyloxy and benzyloxy,
or is trialkylsilylalkoxy, aryldialkylsilyloxy, aralkyldialkylsilyloxy, diarylalkylsilyloxy, diaralkylalkylsilyloxy, a radical of the formula NR'R', in which the radicals R' are identical or different radicals from the group comprising alkyl, alkenyl, alkynyl and cycloalkyl, or is pyridino, morpholino, dialkylmorpholino, hydrazino or
a radical of the formula

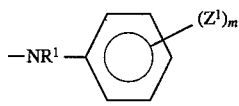

in which $R^1$ is a hydrogen atom, alkyl, alkenyl or alkynyl and the radicals $Z^1$ independently of one another are halogen, nitro, alkyl, alkenyl, alkoxy or phenoxy and m is an integer from 0 to 5, or
is a radical of the formula

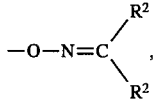

in which the radicals $R^2$ in each case independently of one another are alkyl, or together with the carbon atom linking them are cycloalkyl, or is

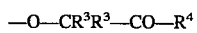

in which the $R^3$ radicals independently of one another are hydrogen, alkyl, alkenyl, alkynyl, aryl, benzyl, alkoxy, alkenyloxy, alkynyloxy or phenoxy and $R^4$ is hydrogen, alkyl, alkenyl, alkynyl, aryl or benzyl, or
is a radical of the formula

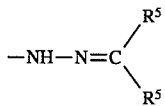

in which the $R^5$ radicals independently of one another are alkyl, hydrogen or aryl, or together with the carbon atom linking them are cycloalkyl, or
is a radical of the formula

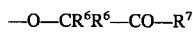

in which the radicals $R^6$ independently of one another are hydrogen, alkyl, alkenyl, alkynyl, aryl, benzyl, alkoxy, alkenyloxy, alkynyloxy or phenoxy and $R^7$ has the meaning given above for R, Z is halogen, nitro, cyano, $(C_1-C_4)$alkyl, $(C_1-C_4)$alkoxy, $(C_1-C_4)$alkylthio, where the alkyl, alkoxy and alkylthio groups independently of one another are unsubstituted or substituted by one or more halogen atoms, in particular fluorine or chlorine, or is $(C_3-C_6)$cycloalkyl which is unsubstituted or substituted by $(C_1-C_4)$alkyl, or amino, hydroxymethyl, $(C_1-C_4)$alkylamino, di$(C_1-C_4)$alkylamino, $(C_1-C_4)$alkoxymethyl, where the alkyl and alkoxy groups in the 3 last-mentioned radicals independently of one another are unsubstituted or substituted by $(C_1-C_4)$alkyl, or is phenyl or phenoxy, where phenyl and phenoxy independently of one another are unsubstituted or monosubstituted or polysubstituted by radicals from the group comprising halogen and trifluoromethyl, and n is an integer from 0 to 5, in particular 0 to 3,
and conventional formulation auxiliaries.

The invention furthermore provides selective herbicidal agents which contain an active ingredient of the formula (I) mentioned or salts thereof, in combination with a herbicide and, if desired, customary formulation auxiliaries.

In the formula (I), alkyl, alkoxy and alkylthio radicals and the corresponding unsaturated radicals can in each case be straight-chain or branched and preferably have less than 5 carbon atoms. Halogen is fluorine, chlorine, bromine or iodine, preferably fluorine, chlorine or bromine, in particular fluorine or chlorine.

In the case where Z=OH, the compounds of the formula (I) can form salts. Salts which can be employed according to the invention are those which can be used in agriculture. Suitable salts are, for example, metal salts such as alkali metal salts or alkaline earth metal salts, in particular sodium salts or potassium salts, salts with ammonium, mono-, di-, tri- or tetra-$(C_1-C_4)$alkylammonium or with mono-, di-, tri- or tetra-$(C_{1-4})$alkanolammonium.

In particular, the invention also provides all stereoisomers and their mixtures which are embraced by the formula (I) but are not specifically defined. Stereoisomers can mainly occur when one or more asymmetric carbon atoms and/or suitably substituted double bonds are present in the compounds of the formula (I). The stereoisomers can be obtained from racemic mixtures by customary separation methods. Alternatively, stereoisomers can be selectively prepared by employing stereoselective reactions using optically active starting substances.

Plant-protecting or selective herbicidal agents according to the invention which are of particular interest are those which contain a compound of the formula (I) mentioned in which R is OH, SH, $(C_1-C_4)$alkoxy, $(C_2-C_4)$alkenyloxy, $(C_2-C_4)$alkynyloxy, $(C_1-C_4)$alkylthio, $(C_2-C_4)$alkenylthio, $(C_2-C_4)$alkynylthio, $(C_3-C_8)$cycloalkoxy or $(C_3-C_8)$cycloalkylthio, where the 8 last-mentioned groups are unsubstituted or monosubstituted or polysubstituted by radicals from the group comprising phenyl, $(C_1-C_4)$alkoxy, $(C_2-C_4)$alkenyloxy, $(C_2-C_4)$alkynyloxy, benzyloxy, phenyloxy, $(C_3-C_8)$cycloalkyloxy, $(C_1-C_4)$alkylthio, mono- and di-$(C_1-C_4)$alkylamino, cyano, halogen and $NO_2$, or is phenyloxy, phenylthio, benzyloxy or benzylthio, where the 4 last-mentioned groups are unsubstituted or substituted by 1 to 3 radicals from the group comprising $(C_1-C_4)$ alkyl, $(C_2-C_4)$alkenyl, $(C_2-C_4)$alkynyl, halogen, cyano, $NO_2$, $(C_1-C_4)$alkoxy, $(C_2-C_4)$alkenyloxy, $(C_2-C_4)$alkynyloxy, $(C_1-C_4)$alkylthio, mono- and di-$(C_1-C_4)$alkylamino, phenyloxy and benzyloxy, or is a radical of the formula —NR'R' in which R' is $(C_1-C_4)$alkyl, or is pyridino, morpholino, dimethylmorpholino, hydrazino or a radical of the formula

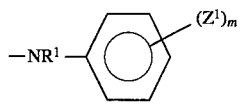

in which R is hydrogen or $(C_1-C_4)$alkyl, the radicals $Z^1$ independently of one another are halogen, nitro, $(C_1-C_4)$alkyl, $(C_1-C_4)$alkoxy or phenoxy, and m is 0 to 3, or is a radical of the formula $-O-N=CR^2R^2$ in which the $R^2$ radicals are $(C_1-C_4)$alkyl, in particular methyl, or together with the carbon atom linking them are cyclohexyl or cyclopentyl, or is a radical of the formula $-O-CR^3R^3-CO-R^4$ in which the $R^3$ radicals independently of one another are hydrogen, $(C_1-C_4)$alkyl, $(C_2-C_4)$alkenyl, $(C_2-C_4)$alkynyl, phenyl, benzyl or $(C_1-C_4)$alkoxy and $R^4$ is $(C_1-C_4)$alkyl, $(C_2-C_4)$alkenyl, $(C_2-C_4)$alkynyl, phenyl or benzyl, or is a radical of the formula $-NH-N=CR^5R^5$ in which the $R^5$ radicals independently of one another are hydrogen, $(C_{1-4})$alkyl or phenyl, or together with the carbon atom linking them are cyclohexyl or cyclopentyl, or is a radical of the formula $-O-CR^6R^6-CO-R^7$ in which the $R^6$ radicals independently of one another are hydrogen, $(C_1-C_4)$alkyl, $(C_2-C_4)$alkenyl, $(C_2-C_4)$alkynyl, phenyl, benzyl or $(C_1-C_4)$alkoxy and $R^7$ has the meaning mentioned for R.

The compounds of Table 1 below are known from the literature, but their safener action has not been recognized to date; cf., for example, Chem. Ber., Vol. 106, 3275 (1973); Zh. Obs. Khim., Vol. 52 (8), 1932–3 (1982); Chem. Pharm. Bull., Vol. 28 (11), 3296 (1980); Tetrahedron Lett., Vol. 25 (19), 2029 (1984); Aust. J. Chem., Vol. 37 (6), 1217 (1984); Tetrahedron, Vol. 40 (15), 2985 (1984); J. Chem. Soc. Chem. Commun., Vol. 1984 (22), 1523–14 (1984); J. Org. Chem., Vol. 52, 2137 (1987); J. Org. Chem., Vol. 53, 2238 (1988); Chem. Ber., Vol. 106, 3345 (1973) and JP-A-62-103070 (1987):

TABLE 1

(Ia)

| $(Z)_n$ | R |
|---|---|
| H | $-OCH_3$ |
| 3-$CH_3$ | $-OCH_3$ |
| 4-$CH_3$ | $-OCH_3$ |
| 2,3-$Cl_2$ | $-OCH_3$ |
| 2,4-$Cl_2$ | $-OCH_3$ |
| 4,5-$Cl_2$ | $-OCH_3$ |
| 3-$OC_6H_5$ | $-OCH_3$ |
| 4-$OCF_2Br$ | $-OCH_3$ |
| 4-$OCF_3$ | $-OCH_3$ |
| 2-Cl, 5-$NO_2$ | $-OCH_3$ |
| 4-Phenoxyphenyl | $-OCH_3$ |
| 3-$CF_3$ | $-OCH_3$ |
| 3-Cl, 4-F | $-OCH_3$ |
| 2,6-$Cl_2$ | $-OCH_3$ |
| 3-$OCF_2H$ | $-OCH_3$ |
| 3-F | $-OCH_3$ |
| 4-$CF_3$ | $-OCH_3$ |
| 5,6-$Cl_2$ | $-OCH_3$ |
| 4,6-$Cl_2$ | $-OCH_3$ |
| 3-Br | $-OCH_3$ |
| 4-CN | $-OCH_3$ |
| 4-F | $-OCH_3$ |
| 4-Br | $-OCH_3$ |
| 3-$NO_2$ | $-OCH_3$ |
| 3,4-$Cl_2$ | $-OCH_3$ |
| 4-$OCHF_2$ | $-OCH_3$ |
| 2-Cl | $-OCH_3$ |
| 4-$NO_2$ | $-OCH_3$ |
| 4-$OCH_3$ | $-OCH_3$ |
| 3,4-$Cl_2$ | OH |
| 4-$CF_3$ | OH |
| 4-Cl | OH |
| H | OH |
| H | $-OC_2H_5$ |
| 4-Cl | $-OC_2H_5$ |
| 4-Cl | $-O$-iso$C_3H_7$ |

The present invention therefore also provides the compounds of the above-defined formula (I), or salts thereof, which were hitherto unknown. These are compounds of the formula (I) or salts thereof, with the exception of compounds of the formula (I) in which X is an oxygen atom, a) R is $OCH_3$ and $(Z)_n$ is H, 3-$CH_3$, 4-$CH_3$, 2,3-$Cl_2$, 2,4-$Cl_2$, 2,6-$Cl_2$, 3,4-$Cl_2$, 4,6-$C_2$, 5,6-$Cl_2$, 3-$OC_6H_5$, 4-$OCF_2Br$, 4-$OCF_3$, 2-Cl-5-$NO_2$, 4-phenoxyphenyl, 3-$CF_3$, 3-Cl-4-F, 3-$OCF_2H$, 3-F, 4-$CF_3$, 3-Br, 4-CN, 4-F, 4-Br, 3-$NO_2$, 3,4-$Cl_2$, 4-$OCHF_2$, 2-Cl, 4-$NO_2$, 4-$CH_3$ or 4-$OCH_3$, b) R is $OC_2H_5$ and $(Z)_n$ is H or 4-Cl, c) R is OH and $(Z)_n$ is 3,4-$Cl_2$, 4-$CF_3$, 4-Cl or H, or d) R is i-$OC_3H_7$ and $(Z)_n$ is 4-Cl.

The compounds of the formula (I) which are known and those which were hitherto unknown can be prepared by, or analogously to, the methods described in the literature cited. For example, compounds of the formula (I) are obtained by reacting an acrylic acid derivative of the formula (II)

$$H_2C=CH-CO-R \qquad (II)$$

with a compound of the formula (III)

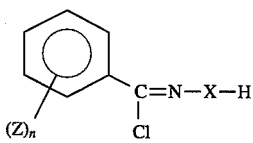

where R, Z, n and X in the formulae (II) and (III) have the meanings mentioned. The reaction is preferably carried out in an aprotic, dipolar organic solvent such as ether at −10° C. up to the boiling point of the solvent and in the presence of an organic base such as triethylamine or pyridine or an inorganic base such as potassium carbonate, sodium carbonate or sodium bicarbonate.

The compounds of the formulae (II) and (III) are known or can be prepared by generally known processes (see, for example, J. Am. Chem. Soc., Vol. 46, 731 (1924); Angew. Chem., Vol. 75, 604 (1963)).

The compounds of the formula (I) reduce or prevent phytotoxic side effects of plant protection agents, in particular of herbicides, which can occur when these agents are employed in crops.

The compounds of the formula (I) can be applied in succession or together with the herbicidal active ingredients. They are then capable of reducing or completely eliminating harmful side effects of the herbicides in crop plants, without impairing the effectiveness of these herbicides against harmful plants.

This makes it possible to considerably enlarge the field of application of conventional herbicides. Compounds which possess the property of protecting crop plants against phytotoxic damage by herbicides are called "antidotes" or "safeners".

Examples of herbicides whose phytotoxic side effects can be reduced by means of the compounds of the formula (I) are carbamates, thiocarbamates, haloacetanilides, substituted phenoxy-, naphthoxy- and phenoxyphenoxycarboxylic acid derivatives as well as heteroaryloxyphenoxycarboxylic acid derivatives, such as quinolyloxy-, quinoxalyloxy-, pyridyloxy-, benzoxazolyloxy-, benzothiazolyloxyphenoxycarboxylic acid esters, and furthermore dimedone oxime derivatives. Preferred compounds amongst these are phenoxyphenoxy- and heteroaryloxyphenoxyalkanecarboxylic acid esters. Suitable esters in this connection are, in particular, lower alkyl, alkenyl and alkynyl esters.

The following herbicides may be mentioned by way of example but without imposing any restrictions:

A) herbicides of the $(C_1-C_4)$alkyl, $(C_2-C_4)$alkenyl and $(C_3-C_4)$alkynyl phenoxyphenoxy- and heteroaryloxyphenoxycarboxylate type, such as
methyl 2-(4-(2,4-dichlorophenoxy)phenoxy)propionate,
methyl 2-(4-(4-bromo-2-chlorophenoxy)phenoxy)propionate,
methyl 2-(4-(4-trifluoromethylphenoxy)phenoxy)propionate,
methyl 2-(4-(2-chloro-4-trifluoromethylphenoxy)phenoxy)propionate,
methyl 2-(4-(2,4-dichlorobenzyl)phenoxy)propionate,
ethyl 4-(4-(4-trifluoromethylphenoxy)phenoxy)pent-2-enoate,
ethyl 2-(4-(3,5-dichloropyridyl-2-oxy)phenoxy)propionate,
propargyl 2-(4-(3,5-dichloropyridyl-2-oxy)phenoxy)propionate,
ethyl 2-(4-(6-chlorobenzoxazol-2-yloxy)phenoxy)propionate,
methyl 2-(4-(3-chloro-5-trifluoromethyl-2-pyridyloxy)phenoxy)propionate,
butyl 2-(4-(5-trifluoromethyl-2-pyridyloxy)phenoxy)propionate,
methyl 2-(4-(3-fluoro-5-chloropyridyl-2-oxy)phenoxy)propionate,
propargyl 2-(4-(3-fluoro-5-chloropyridyl-2-oxy)phenoxy)propionate,
methyl 2-(4-(6-chloro-2-quinoxalyloxy)phenoxy)propionate,
methyl 2-(4-(6-fluoro-2-quinoxalyloxy)phenoxy)propionate,
methyl 2-(4-(6-chloro-2-quinolyloxy)phenoxy)propionate and
8-methoxycarbonylmethyl 2-(4-(5-chloro-3-fluoropyridin-2-yl)phenoxy)thiopropionate B) chloroacetanilide herbicides, such as
N-(3'-methoxyprop-2'-yl)methyl-6-ethylchloroacetanilide,
N-(3-methyl-1,2,4-oxadiazol-5-ylmethyl)-2',6'-dimethylchloroacetanilide, C) thiocarbamates, such as
S-ethyl N,N-dipropylthiocarbamate or
S-ethyl N,N-diisobutylthiocarbamate, D) dimedone derivatives, such as
methyl 3-(1-allyloxyimino)butyl-4-hydroxy-6,6-dimethyl-2-oxocyclohex-3-enecarboxylate
2-(N-ethoxybutyrimidoyl)-5-(2-ethylthiopropyl)-3-hydroxy-2-cyclohexen-1-one,
2-(N-ethoxybutyrimidoyl)-5-(2-phenylthiopropyl)-3-hydroxy-2-cyclohexen-1-one,
2-(1-allyloxyiminobutyl)-4-methoxycarbonyl-5,5-dimethyl-3-oxocyclohexenol,
2-(1-(3-chloroallyloxy)iminobutyl)-5-(2-ethylthio)propyl)-3-hydroxycyclohex-2-enone propyl)-2-(1-(ethoxyimino)butyl)-3-hydroxy-5-(thian-3-yl)cyclohex-2-enone or
2-(1-ethoxyiminopropyl)-5-(2,4,6-trimethylphenyl)-3-hydroxy-2-cyclohexen-1-one.

The ratio of safener:herbicide can vary within wide limits, in the range between 1:10 and 10:1, in particular between 2:1 and 1:10. The amounts of herbicide and safener which are ideal in each case depend on the type of the herbicide used or on the safener used as well as on the nature of the plant stand to be treated, and can be determined in each individual case by appropriate experiments.

The safeners are mainly employed in particular in cereal crops (wheat, rye, barley, oats), rice, maize and sorghum, but also in cotton, sugar beet, sugar cane and soya bean.

Depending on their properties, the safeners of the formula (I) can be used for pre-treating the seed of the crop plant (seed dressing), or can be incorporated into the seed furrows prior to sowing, or used together with the herbicide prior to, or after, plant emergence. Pre-emergence treatment includes both the treatment of the area under cultivation prior to sowing and the treatment of the areas under cultivation where seed has been sown but emergence of the crop plants has not yet taken place. Application together with the herbicide is preferred. Tank mixes or readymixes can be employed for this purpose.

Depending on the indication and the herbicide used, the application rates required of the compounds of the formula (I) can vary within wide limits and are generally between 0.01 and 10 kg of active ingredient per hectare.

The present invention therefore also relates to a method of protecting crop plants against phytotoxic side effects of herbicides, which comprises applying an effective amount of a compound of the formula (I) before, after, or simultaneously with, the herbicide.

Moreover, the compounds according to the invention have growth-regulatory properties in crop plants. They engage in the plant metabolism in a regulating manner and can therefore be employed for simplifying harvesting, for example by triggering desiccation, abscission and stunted growth. Moreover, they are also suitable for generally controlling and inhibiting undesired vegetative growth, without destroying the plants in the process. Inhibition of vegetative growth is highly important in many monocotyledon and dicotyledon crops since lodging can be reduced, or prevented completely, by this method.

The compounds of the formula (I) or their combinations with one or more of the herbicides or groups of herbicides mentioned can be formulated in a variety of ways, as predetermined by the biological and/or chemicophysical parameters. The following formulation possibilities are therefore suitable: wettable powders (WP), emulsifiable concentrates (EC), aqueous solutions (SL), concentrated emulsions such as oil-in-water and water-in-oil emulsions (EW), sprayable solutions or emulsions, oil- or water-based dispersions (SC), dusting agents (DP), seed-dressing agents, soil granules or granules for broadcasting (FG), water-dispersible granules (WG), ULV formulations, microcapsules or waxes.

These individual formulation types are known in principle and are described, for example, in: Winnacker-Küchler, "Chemische Technologie" [Chemical Technology], Volume 7, C. Hauser Verlag, Munich, 4th Ed., 1986; van Valkenburg, "Pesticides Formulations", Marcel Dekker, N.Y., 2nd Ed. 1972–73; K. Martens, "Spray Drying Handbook", 3rd Ed. 1979, G. Goodwin Ltd., London.

The formulation auxiliaries necessary such as inert materials, surfactants, solvents and other additives, are also known and are described, for example, in: Watkins, "Handbook of Insecticide Dust Diluents and Carriers", 2nd Ed., Darland Books, Caldwell, N.J.; H.v.Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart, 1976; Winnacker-Küchler, "Chemische Technologie" [Chemical Technology], Volume 7, C. Hauser Verlag, Munich, 4th Ed., 1986.

Combinations with other pesticidally active ingredients, fertilizers and/or growth regulators may also be prepared on the basis of these formulations, for example in the form of a readymix or as a tank mix.

Wettable powders are preparations which are uniformly dispersible in water and which, besides the active ingredient, also contain wetting agents, for example polyoxyethylated alkylphenols, polyoxyethylated fatty alcohols or fatty amines, alkanesulfonates or alkylarylsulfonates, and dispersants, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active ingredient in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products (for example block copolymers), alkyl polyglycol ethers, sorbitan fatty acid esters, polyoxyethylene sorbitan fatty acid esters or polyoxyethylene sorbitol esters.

Dusting agents can be obtained by grinding the active ingredient with finely divided solid substances, for example talc or natural clays, such as kaolin, bentonite, pyrophillite or diatomaceous earth.

Soil granules or granules for broadcasting can be produced either by spraying the active ingredient onto adsorptive, granulated inert material or by applying active ingredient concentrates onto the surface of carriers, such as sand, kaolinites or granulated inert material, by means of adhesives, for example polyvinyl alcohol, sodium polyacrylate or, alternatively, mineral oils. Suitable active ingredients can also be granulated in the manner which is conventional for the production of fertilizer granules, if desired in a mixture with fertilizers.

As a rule, the agrochemical preparations contain 0.1 to 99 percent by weight, in particular 0.1 to 95% by weight, of active ingredient of the formula (I), or of active ingredient mixture with antidote/herbicide, 1 to 99.9% by weight, in particular 5 to 99.8% by weight, of a solid or liquid additive, and 0 to 25% by weight, in particular 0.1 to 25% by weight, of a surfactant.

The concentration of active ingredient in wettable powders is, for example, about 10 to 90% by weight, the remainder to 100% by weight being composed of conventional formulation components. In the case of emulsifiable concentrates, the concentration of active ingredients can be about 1 to 80% by weight, preferably 5 to 80% by weight. Formulations in the form of dusts usually contain 1 to 25% by weight, preferably 5 to 20% by weight, of active ingredient, sprayable solutions about 0.2 to 25% by weight, preferably 2 to 20% by weight, of active ingredient. In the case of water-dispersible granules, the active ingredient content depends partly on whether the active compound is liquid or solid. The water-dispersible granules generally contain between 10 and 90% by weight of active ingredient.

In addition, the active ingredient formulations mentioned contain, if appropriate, the adhesives, wetting agents, dispersants, emulsifiers, penetrants, solvents, fillers or carriers which are conventional in each case.

For use, the formulations, in commercially available form, are diluted, if appropriate, in a customary manner, for example using water in the case of wettable powders, emulsifiable concentrates, dispersions and water-dispersible granules. Preparations in the form of dusts, soil granules and granules for broadcasting and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active substance, but is preferably between 0.01 and 5 kg/ha.

The examples which follow serve to illustrate the invention in greater detail.

A. Formulation Examples a) A dusting agent is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as the wetting agent and dispersant, and grinding the mixture in a pinned disk-mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
 75 parts by weight of a compound of the formula I,
 10 parts by weight of calcium ligninsulfonate,
 5 parts by weight of sodium lauryl sulfate,
 3 parts by weight of polyvinyl alcohol and
 7 parts by weight of kaolin,
grinding the mixture in a pinned disk mill and granulating the powder in a fluidized bed by spraying on water as the granulation liquid.

f) Water-dispersible granules are also obtained by homogenizing and precomminuting
 25 parts by weight of a compound of the formula (I),
 5 parts by weight of sodium 2,2'-dinaphthylmethane-6,6'-disulfonate,
 2 parts by weight of sodium oleoylmethyltaurinate,
 1 part by weight of polyvinyl alcohol,
 17 parts by weight of calcium carbonate and
 50 parts by weight of water,
in a colloid mill, subsequently grinding the mixture in a bead mill, and atomizing and drying the resulting suspension in a spray tower by means of a single-fluid nozzle.

g) Analogously to the above formulations, formulations of selective herbicidal agents are obtained when a mixture of an active ingredient of the formula (I) with a herbicide such as, for example, fenoxapropethyl, is employed instead of the active ingredient of the formula (I).

B) Chemical Examples

Ethyl 3-(2-methoxyphenyl)-2-isoxazoline-5-carboxylate (Example 78, see Table 2)

50 ml of ethyl acrylate and 4.04 g of triethylamine are introduced into a reaction vessel. 7.4 g of 2-methoxyphenylhydroxamyl chloride in 200 ml of ether are added dropwise to this mixture at 0° C. The mixture is stirred for three hours at room temperature, 50 ml of water are then added and the mixture is extracted with ether. The extract is dried over $MgSO_4$, and the ether is then distilled off and the crude product is purified on a silica gel column (eluent:n-heptane:ethyl acetate=8:2). In this manner, 8.4 g (84% of theory) of the mixed product having a refractive index of $n^{20}_D=1.544$ are obtained.

The derivatives in Table 2 which follows are obtained analogously.

TABLE 2

| Example No. | $(Z)_n$ | R | X | m.p./ $n^{20}_D$ |
|---|---|---|---|---|
| 1 | H | OH | O | 197° C. |
| 2 | " | $OCH_3$ | " | 73° C. |
| 3 | " | $OC_2H_5$ | " | 1.5457 |
| 4 | " | $n-OC_3H_2$ | " | |
| 5 | " | $i-OC_3H_7$ | " | 1.5335 |
| 6 | " | $n-OC_4H_9$ | " | |
| 7 | " | $O-CH_2CO_2C_2H_5$ | " | |
| 8 | " | $O-C_6H_5$ | " | |
| 9 | " | $O-CH_2C_6H_5$ | " | |
| 10 | " | $OCH_2CH=CH_2$ | " | |
| 11 | " | $OCH_2C\equiv CH$ | " | |
| 12 | " | $O-CH_2Si(CH_3)_3$ | " | |
| 13 | " | $O^-K^+$ | " | |
| 14 | 2-Cl | OH | " | |
| 15 | " | $OCH_3$ | " | 1.5609 |
| 16 | " | $OC_2H_5$ | " | 1.5519 |
| 17 | " | $n-OC_3H_7$ | " | |
| 18 | " | $i-OC_3H_7$ | " | |
| 19 | " | $n-OC_4H_9$ | " | |
| 20 | " | $O-CH_2CO_2C_2H_5$ | " | |
| 21 | " | $OC_6H_5$ | " | |
| 22 | " | $OCH_2C_6H_5$ | " | |
| 23 | " | $O-CH_2CH=CH_2$ | " | |
| 24 | " | $O-CH_2C\equiv CH$ | " | |
| 25 | " | $O-CH_2Si(CH_3)_3$ | " | |
| 26 | " | $O^-K^+$ | " | |
| 27 | 4-Cl | OH | O | |
| 28 | " | $OCH_3$ | " | 75° C. |
| 29 | " | $OC_2H_5$ | " | 68° C. |
| 30 | " | $n-OC_3H_7$ | " | |
| 31 | " | $i-OC_3H_7$ | " | |
| 32 | " | $n-OC_4H_9$ | " | |
| 33 | " | $O-CH_2CO_2C_2H_5$ | " | |
| 34 | " | $O-C_6H_5$ | " | |
| 35 | " | $O-CH_2C_6H_5$ | " | |
| 36 | " | $O-CH_2CH=CH_2$ | " | |
| 37 | " | $O-CH_2C\equiv CH$ | " | |
| 38 | " | $O-CH_2Si(CH_3)_3$ | " | |
| 39 | 2,4-$Cl_2$ | OH | " | |
| 40 | " | $OCH_3$ | " | 58° C. |
| 41 | " | $OC_2H_5$ | " | 64° C. |
| 42 | " | $OC_3H_7$ (n) | " | |
| 43 | " | $OC_3H_7$ (iso) | " | |
| 44 | " | $OC_4H_9$ (n) | " | |
| 45 | " | $O-CH_2CO_2C_2H_5$ | " | 38° C. |
| 46 | " | $OC_6H_5$ | " | |
| 47 | " | $OCH_2C_6H_5$ | " | |
| 48 | " | $O-CH_2CH=CH_2$ | " | |
| 49 | " | $O-CH_2C\equiv CH$ | " | |
| 50 | " | $O-CH_2Si(CH_3)_3$ | " | |
| 51 | " | $OCH_2CO_2CH_3$ | " | oil |
| 52 | 2,6-$Cl_2$ | OH | " | 140° C. |
| 53 | " | $OCH_3$ | " | 1.5541 |
| 54 | " | $OC_2H_5$ | " | 1.5372 |
| 55 | " | $OC_3H_7$ (n) | " | |
| 56 | " | $OC_3H_7$ (iso) | " | |
| 57 | " | $OC_4H_9$ (n) | " | 1.5302 |
| 58 | 2,6-$Cl_2$ | $O-CH_2CO_2C_2H_5$ | O | |
| 59 | " | $O-C_6H_5$ | " | |
| 60 | " | $O-CH_2C_6H_5$ | " | |
| 61 | " | $O-CH_2CH=CH_2$ | " | 1.5472 |
| 62 | " | $O-CH_2C\equiv CH$ | " | 67° C. |

TABLE 2-continued

[Structure: phenyl ring with (Z)n substituent, connected to C(=N-X)-CH2-CH(R')-C(=O)-R group]

| Example No. | (Z)n | R | X | m.p./$n_D^{20}$ |
|---|---|---|---|---|
| 63 | " | O—CH₂Si(CH₃)₃ | " | |
| 64 | 4-OCH₃ | OH | " | |
| 65 | " | OCH₃ | " | 75° C. |
| 66 | " | OC₂H₅ | " | 1.5535 |
| 67 | " | OC₃H₇ (n) | " | |
| 68 | " | OC₃H₇ (iso) | " | |
| 69 | " | OC₄H₉ (n) | " | |
| 70 | " | O—CH₂CO₂C₂H₅ | " | |
| 71 | " | OC₆H₅ | " | |
| 72 | " | OCH₂C₆H₅ | " | |
| 73 | " | O—CH₂CH=CH₂ | " | |
| 74 | " | O—CH₂C≡CH | " | |
| 75 | " | O—CH₂Si(CH₃)₃ | " | |
| 76 | 2-OCH₃ | OH | " | |
| 77 | " | OCH₃ | " | oil |
| 78 | " | OC₂H₅ | " | 1.544 |
| 79 | " | OC₃H₇ (n) | " | |
| 80 | " | OC₃H₇ (iso) | " | |
| 81 | " | OC₄H₉ (n) | " | |
| 82 | " | O—CH₂CO₂C₂H₅ | " | |
| 83 | " | O—C₆H₅ | " | |
| 84 | " | O—CH₂C₆H₅ | " | |
| 85 | " | O—CH₂CH=CH₂ | " | |
| 86 | " | O—CH₂C≡CH | " | |
| 87 | " | O—CH₂Si(CH₃)₃ | " | |
| 88 | 2-CH₃ | OH | " | |
| 89 | " | OCH₃ | " | |
| 90 | " | OC₂H₅ | " | |
| 91 | " | OC₃H₇ (n) | " | |
| 92 | " | OC₃H₇ (iso) | " | |
| 93 | " | OC₄H₉ (n) | " | |
| 94 | " | O—CH₂OC₂H₅ | " | |
| 95 | " | OC₆H₅ | " | |
| 96 | " | OCH₂C₆H₅ | " | |
| 97 | " | O—CH₂CH=CH | " | |
| 98 | " | O—CH₂C≡CH | " | |
| 99 | " | O—CH₂Si(CH₃)₃ | " | |
| 100 | H | OCH₃ | S | |
| 101 | " | OC₂H₅ | " | |
| 102 | 4-Cl | OCH₃ | " | |
| 103 | " | OC₂H₅ | " | |
| 104 | 2,4-Cl₂ | OCH₃ | " | |
| 105 | " | OC₂H₅ | " | |
| 106 | 2,6-Cl₂ | OCH₃ | " | |
| 107 | " | OC₂H₅ | " | |
| 108 | 4-OCH₃ | OCH₃ | " | |
| 109 | " | OC₂H₅ | " | |
| 110 | 2-OCH₃ | OCH₃ | " | |
| 111 | " | OC₂H₅ | " | |
| 112 | 2-CH₃ | OCH₃ | " | |
| 113 | " | OC₂H₅ | " | |
| 114 | 2-Cl | N(CH₃)₂ | O | |
| 115 | " | NHNH₂ | " | |
| 116 | " | NH₂ | " | |
| 117 | 2,4-Cl₂ | N(CH₃)₂ | O | |
| 118 | " | NHNH₂ | " | |
| 119 | " | NH₂ | " | |
| 120 | 4-Cl | N(CH₃)₂ | " | |
| 121 | " | NHNH₂ | " | |
| 122 | " | NH₂ | " | |

C) Biological Examples

Example 1

In the greenhouse, wheat and barley were grown in plastic pots until they had reached the 3–4 leaf stage and then treated in succession with compounds according to the invention and herbicides using the post-emergence method. For this purpose, the herbicides and the compounds of the formula (I) were applied in the form of aqueous suspensions or emulsions at a water application rate of 600 to 800 1/ha (converted). 3–4 weeks after the treatment, the plants were scored visually for any type of damage by the herbicides which had been applied, the extent of sustained growth inhibition being particularly taken into account. The plants were assessed in percentages in comparison with untreated controls.

The results from Table 3 demonstrate that the compounds according to the invention are capable of effectively reducing severe herbicide damage on crop plants.

Even when the herbicide H is applied at excessive dosage rates, severe damage which occurs on the crop plants is markedly reduced, and minor damage is prevented completely. Mixtures of herbicides and compounds according to the invention are therefore outstandingly suitable for selectively controlling weeds in cereal crops.

TABLE 3

Safener action of the compounds according to the invention

| Ex. No. | kg of a.i./ha | TRAE | HOVU |
|---|---|---|---|
| H | 2.0 | 80 | — |
|  | 0.2 | — | 85 |
| H + 40 | 2.0 + 1.25 | 20 | — |
| H + 40 | 0.2 + 1.25 | — | 30 |
| H + 41 | 2.0 + 1.25 | 25 | — |
| H + 41 | 0.2 + 1.25 | — | 35 |

Abbreviations:
TRAE = *Triticum aestivum*
HOVU = *Hordeum vulgare*
a.i. = active ingredient
H = ethyl 2-(4-(6-chlorobenzoxazol-2-yloxy)-phenoxypropionate (fenoxaprop-ethyl)

We claim:

1. A herbicidal and crop-plant-protecting composition which contains an effective amount of a safener compound of the formula (I), or a salt thereof,

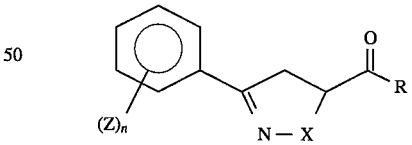

in which:

X is an oxygen or sulfur atom,

R is OH, SH, alkoxy, alkenyloxy, alkynyloxy, alkylthio, alkenylthio, alkynylthio, cycloalkyloxy or cycloalkylthio, where the 8 last-mentioned groups are unsubstituted or mono- or polysubstituted by radicals from the group comprising phenyl, alkoxy, alkenyloxy, alkynyloxy, benzyloxy, phenyloxy, cycloalkyloxy, alkylthio, mono- and dialkylamino, cyano, halogen and $NO_2$, or is benzyloxy, phenyloxy, benzylthio or phenylthio, where the 4 last-mentioned groups are unsubstituted or mono- or polysubstituted by radicals from the group comprising alkyl, alkenyl, alkynyl, halogen, cyano, $NO_2$, alkoxy, alkenyloxy, alkynyloxy, alkylthio, mono- and dialkylamino, phenyloxy and benzyloxy, or is trialkylsilylalkoxy, aryldialkylsilyloxy, aralkyldialkylsilyloxy, diarylalkylsilyloxy, diaralkylalkylsilyloxy, a radical of the formula NR'R', in which the radicals R' are identical or different radicals from the group comprising alkyl, alkenyl, alkynyl and cycloalkyl, or is pyridino, morpholino, dialkylmorpholino, hydrazino or a radical of the formula

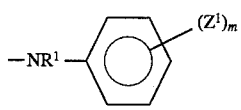

in which $R^1$ is a hydrogen atom, alkyl, alkenyl or alkynyl and the radicals $Z^1$ independently of one another are halogen, nitro, alkyl, alkenyl, alkoxy or phenoxy and m is an integer from 0 to 5, or is a radical of the formula

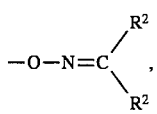

in which the radicals $R^2$ in each case independently of one another are alkyl, or together with the carbon atom linking them are cycloalkyl, or is

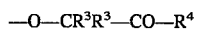

in which the $R^3$ radicals independently of one another are hydrogen, alkyl, alkenyl, alkynyl, aryl, benzyl, alkoxy, alkenyloxy, alkynyloxy or phenoxy and $R^4$ is hydrogen, alkyl, alkenyl, alkynyl, aryl or benzyl, or is a radical of the formula

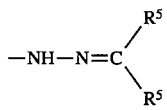

in which the $R^5$ radicals independently of one another are alkyl, hydrogen or aryl, or together with the carbon atom linking them are cycloalkyl, or is a radical of the formula

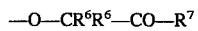

in which the radicals $R^6$ independently of one another are hydrogen, alkyl, alkenyl, alkynyl, aryl, benzyl, alkoxy, alkenyloxy, alkynyloxy or phenoxy and $R^7$ has the meaning given above for R, Z is halogen, nitro, cyano, $C_1-C_4$)alkyl, $(C_1-C_4)$alkoxy, $C_1-C_4$)alkylthio, where the alkyl, alkoxy and alkylthio groups independently of one another are unsubstituted or substituted by one or more halogen atoms, or is $(C_3-C_6)$ cycloalkyl which is unsubstituted or substituted by $C_1-C_4$)alkyl, or amino, hydroxymethyl, $(C_1-C_4)$alkylamino, di$(C_1-C_4)$alkylamino, $(C_1-C_4)$alkoxymethyl, where the alkyl and alkoxy groups in the 3 last-mentioned radicals independently of one another are unsubstituted or substituted by $(C_1-C_4)$alkyl, or is phenyl or phenoxy, where phenyl and phenoxy independently of one another are unsubstituted or monosubstituted or polysubstituted by radicals from the group comprising halogen and trifluoromethyl, and n is an integer from 0 to 5, and an effective amount of one or more herbicides which have herbicidal effect against weeds and which as single agents have phytotoxic side effects towards crop plants and which herbicides are selected from the group consisting of carbamates, thiocarbamates, haloacetanilides, substituted phenoxycarboxylic acid derivatives, substituted naphthoxycarboxylic acid derivatives, phenoxyphenoxy-alkanecarboxylic acid derivatives, heteroaryloxyphenoxy-alkanecarboxylic acid derivatives and dimedone oxime derivatives.

2. A method for controlling undesired plants in crops of useful plants, which comprises applying an effective amount of a herbicide in combination with an effective amount of a safener compound of formula (I), or a salt thereof, to the plants, seeds of the plants or the area under cultivation, wherein the herbicide/safener combination is defined as in claim 1.

3. A method as claimed in claim 2 wherein in formula (I):

X is an oxygen atom,

R is OH, $(C_1-C_4)$ alkyl or $(C_1-C_4)$alkoxy,

Z is halogen, $(C_1-C_4)$ alkoxy, $(C_2-C_4)$alkenyloxy, $(C_2-C_4)$ alkynyloxy or $(C_1-C_4)$alkoxycarbonyl-methoxy, n is 0, 1 or 2, and wherein the herbicide is selected from the group consisting of phenoxyphenoxy- and heteroaryloxyphenoxyalkanecarboxylic acid derivatives.

4. A method for protecting useful plants against phytotoxic side effects of herbicides, which comprises applying the herbicide in combination with an effective amount of a safener compound of formula (I), or a salt thereof, to the plants, seeds of the plants or the area under cultivation, wherein the herbicide/safener combination is defined as in claim 1.

5. A method as claimed in claim 2 wherein in formula (I):

X is an oxygen atom,

R is OH, $(C_1-C_4)$alkyl or $(C_1-C_4)$alkoxy,

Z is halogen, $(C_1-C_4)$alkoxy, $(C_2-C_4)$alkenyloxy, $(C_2-C_4)$alkynyloxy or $(C_1-C_4)$alkoxycarbonyl-methoxy, n is 0, 1 or 2, and wherein the herbicide is selected from the group consisting of phenoxyphenoxy- and heteroaryloxyphenoxyalkanecarboxylic acid derivatives.

6. An composition as claimed in claim 1, in which

R is OH, SH, $(C_1-C_4)$alkoxy, $(C_2-C_4)$alkenyloxy, $(C_2-C_4)$alkynyloxy, $(C_1-C_4)$alkylthio, $(C_2-C_4)$alkenylthio, $(C_2-C_4)$alkynylthio, $(C_3-C_8)$cycloalkoxy or $(C_3-C_8)$cycloalkylthio, where the 8 last-mentioned groups are unsubstituted or monosubstituted or polysubstituted by radicals from the group comprising phenyl, $(C_1-C_4)$ alkoxy, $(C_2-C_4)$alkenyloxy, $(C_2-C_4)$ alkynyloxy, benzyloxy, phenyloxy, $(C_3-C_8)$cycloalkyloxy, $(C_1-C_4)$alkylthio, mono- and di-$(C_1-C_4)$alkylamino, cyano, halogen and $NO_2$, or is a radical of the formula —O—$CR^6R^6$—CO—$R^7$ in which the $R^6$ radicals independently of one another are hydrogen, $(C_1-C_4)$alkyl, $(C_2-C_4)$alkenyl, $(C_2-C_4)$alkynyl, phenyl, benzyl or $(C_1-C_4)$ alkoxy and $R^7$ has the meaning mentioned for R.

7. An composition as claimed in claim 1, which contains the active ingredient of the formula (I) or a salt thereof and the herbicide in a ratio by weight of from 10:1 to 1:10.

8. A plant-protection composition as claimed in claim 1, wherein

X is an oxygen atom, a) R is OH or $(C_1-C_5)$-alkoxy and $(Z)_n$ is an individual radical in the 2-, 3- or 4- position on the phenyl ring from the group consisting of F, Cl, Br, CN, $OCHF_2$, $CF_3$ and $NO_2$ or $(Z)_n$ is 3-phenoxy, 2,3-, 2,4-, 2,5- or 3,4-$Cl_2$ or 2,4-, 3,4- or 3,5-$Br_2$ or 3-Cl-4-F, 5-Cl-2-$NO_2$, or 2-Cl-5-$NO_2$ or b) R is $OCH_3$ and $(Z)_n$ is H, 3-$CH_3$, 4-$CH_3$, 2,6-, 4,6- or 5,6-$Cl_2$, 4-$OCF_2Br$, 4-$OCF_3$, 4-phenoxy, 4-phenoxyphenyl, 2,4,6-$(OCH_3)_3$ or 2,4,6-$(CH_3)_3$ or c) R is OH or $OC_2H_5$ and $(Z)_n$ is H.

9. A plant-protection composition as claimed in claim 1, wherein

X is an oxygen atom,

R is OH, $(C_1-C_4)$alkyl, $(C_1-C_4)$alkoxy,

Z is halogen, $(C_1-C_4)$alkoxy, $(C_2-C_4)$alkenyloxy, $(C_2-C_4)$alkynyloxy, $(C_1-C_4)$alkoxycarbonyl-methoxy, n is 0, 1 or 2.

10. A plant-protection composition as claimed in claim 1, wherein the herbicide is selected from the group of herbicides consisting of phenoxyphenoxy- and heteroaryloxyphenoxyalkanecarboxylic acid derivatives.

11. A plant-protection composition as claimed in claim 1, wherein the herbicide is fenoxaprop-ethyl.

12. A method as claimed in claim 1, wherein in formula (I)

X is an oxygen atom,

R is OH, $(C_1-C_4)$alkyl, $(C_1-C_4)$alkoxy,

Z is halogen, $(C_1-C_4)$alkoxy, $(C_2-C_4)$alkenyloxy, $(C_2-C_4)$alkynyloxy, $(C_1-C_4)$alkoxycarbonyl-methoxy, n is 0, 1 or 2.

13. A method as claimed in claim 12, wherein the herbicide is selected from the group of herbicides consisting of phenoxyphenoxy- and heteroaryloxyphenoxy-alkanecarboxylic acid derivatives.

14. A method as claimed in claim 13, wherein the herbicide is fenoxaprop-ethyl.

\* \* \* \* \*